United States Patent [19]
Cornwall

[11] Patent Number: 6,069,256
[45] Date of Patent: May 30, 2000

[54] PROCESS FOR THE PREPARATION OF NIZATIDINE

[75] Inventor: Philip Cornwall, Nottingham, United Kingdom

[73] Assignee: KNOLL Aktiengesellschaft, Ludwigshafen, Germany

[21] Appl. No.: 09/254,453

[22] PCT Filed: Aug. 29, 1997

[86] PCT No.: PCT/EP97/04705

§ 371 Date: Mar. 10, 1999

§ 102(e) Date: Mar. 10, 1999

[87] PCT Pub. No.: WO98/11081

PCT Pub. Date: Mar. 19, 1998

[30] Foreign Application Priority Data

Sep. 11, 1996 [GB] United Kingdom .................... 9619000
May 17, 1997 [GB] United Kingdom .................... 9710005

[51] Int. Cl.[7] ................................................ C07D 277/28
[52] U.S. Cl. .............................................................. 548/205
[58] Field of Search ............................................. 548/205

[56] References Cited

U.S. PATENT DOCUMENTS 4,968,808  11/1990  Mosdorf et al. ......................... 548/205
5,541,335   7/1996  Manning ................................. 548/205

FOREIGN PATENT DOCUMENTS 049618   4/1982   European Pat. Off. .

96/17839   6/1996   WIPO .

*Primary Examiner*—Laura L. Stockton
*Attorney, Agent, or Firm*—Keil & Weinkauf

[57] ABSTRACT

The present invention relates to a novel process for the preparation of nizatidine, N-[2-[[[2-(dimethylamino)methyl-4-thiazolyl]methyl]thio]ethyl]-N'-methyl-2-nitro-1,1-ethenediamine, and pharmaceutically acceptable salts thereof, comprising reacting a compound of formula II

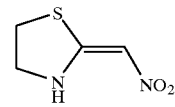

II with a compound of formula III

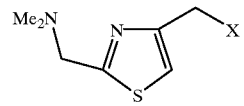

III or a salt thereof, in which X represents a leaving group, in the presence of methylamine in the presence of an inert diluent.

8 Claims, No Drawings

PROCESS FOR THE PREPARATION OF NIZATIDINE

This application is a 371 of PCT/EP97/04705 filed Aug. 29, 1997.

The present invention relates to a novel process for the preparation of nizatidine, N-[2-[[[2-(dimethylamino) methyl-4-thiazolyl]methyl]thio]ethyl]-N'-methyl-2-nitro-1, 1-ethenediamine, and pharmaceutically acceptable salts thereof.

The preparation of nizatidine by fusing 4-chloromethyl-2-dimethylaminomethylthiazole with N-(2-mercaptoethyl)-N'-methyl-2-nitro-1,1-ethenediamine has been suggested generically in EP 49618. However, we have found that N-(2-mercaptoethyl)-N'-methyl-2-nitro-1,1-ethenediamine cannot be isolated and stored. Our attempts to prepare this compound have always produced the disulphide, N-methyl-[N'-[2-(N"-methyl-2-nitro-1,1-ethenediamine) ethyldisulphanyl]ethyl]-2-nitro-1,1-ethenediamine and 3-methylamino-5,6-dihydro-[1,4]-thiazin-2-one oxime.

The present invention provides a novel process for the preparation of nizatidine I

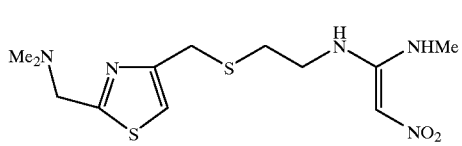

and pharmaceutically acceptable salts thereof, comprising reacting a compound of formula II

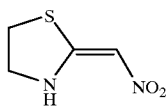

with a compound of formula III

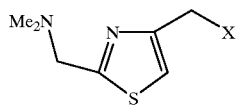

or a salt thereof, in which X represents a leaving group, in the presence of methylamine in the presence of an inert diluent.

The present invention represents a considerable improvement, over the known processes for the preparation of nizatidine, in that it allows a one-pot process with high yields, low production costs, fast processing times and avoids the problems of the known processes. In addition, the process of the present invention allows the possibility of an extremely cost-efficient continuous process.

The reactants involved in this process II, III and methylamine may be mixed in a number of different ways. In one embodiment of the present invention II and III or a salt thereof are combined to give a mixture and methylamine is added to this mixture.

In a second embodiment II is combined with methylamine to give a mixture and III or a salt thereof is added to the mixture. Optionally further methylamine is added as III or a salt thereof is added.

In a third embodiment II, III and methylamine are combined together simultaneously. Optionally further methylamine is added.

The second embodiment is preferred.

In a most preferred embodiment of the present invention the process is continuous and III or a salt thereof is added simultaneously with methylamine to a reaction mixture comprising II and methylamine and after a suitable time period the product is removed and the vessel is re-charged with reactants and the process is continued.

The term inert diluent as used herein means a liquid which is inert to the reactants and products in the process under the conditions used in the process. Any such liquid may be used. Preferably the inert diluent is water or an organic solvent selected from a nitrile, a $C_{1-8}$ alcohol, a halogenated alkane, an ether, N,N-dimethylformamide, dimethyl sulphoxide and mixtures thereof. More preferably the inert diluent is water, acetonitrile, methanol, ethanol, propanol, dichloromethane or tetrahydrofuran or mixtures thereof. Most preferably the inert diluent is acetonitrile or water or mixtures thereof.

Surprisingly it has been found that the process may be carried out in the presence of water. This means that the process may be carried out in inert diluents which do not have to be rigorously dried. In addition aqueous solutions of methylamine may be used which are easier to use on a production scale than gaseous methylamine leading to cost savings.

The tolerance of the process to water also leads to considerable improvements in the physical handling of the materials during the process. The use of water means that a salt of III may be added as a solution at ambient temperature thus eliminating the necessity of heating to keep III in solution during the addition or the necessity of using acidic adjuncts which may corrode the reaction vessels.

The process may be carried out without batchwise addition of starting materials at set time intervals which is costly. Instead a simple continuous addition of reactants may be employed which is convenient to use, easy to control and may be scaled up to give an easy to operate and cost effective production process.

Suitably X represents a leaving group known to those skilled in the art, for example halo or a group of formula $OR_1$ in which $R_1$ represents a) an optionally substituted $C_{1-6}$ alkyl group or an optionally substituted phenyl group or b) a group of formula $SO_2R_2$ or c) a group of formula $COR_2$ or d) a group of formula $CO_2R_2$; in which $R_2$ represents an optionally substituted $C_{1-6}$ alkyl group or an optionally substituted phenyl group. Preferably X represents halo, mesyloxy or tosyloxy. More preferably X represents chloro or bromo.

It will be understood by those skilled in the art that compounds of formula III may be prepared in situ without isolation, from known compounds, for example from the compound of formula III in which X represent hydroxy, by methods known to those skilled in the art.

Suitable salts of the compound of formula III are the hydrochloride, hydrobromide, hydriodide, methanesulphonate, p-toluenesulphonate, sulphate, nitrate, acetate, phosphate, maleate, succinate, citrate, fumarate or tartrate salts. The salts may be mono-salts, e.g. the hydrochloride salt, or di-salts e.g. the dihydrochloride, or non-stoichiometric salts. The salts may be used in the form of solvates for example as hydrates. Preferably the salts are hydrohalide salts particularly the hydrochloride and hydrobromide salts. Most preferably the salt is the dihydrochloride salt.

Suitably the methylamine may be added by bubbling methylamine gas into the inert diluent or alternatively solutions of methylamine in the inert diluent may be added dropwise.

The compound of formula III or a salt thereof may be added as a slurry in the inert diluent, as a solution in the inert diluent or as a dry solid.

Suitably the process is carried out at a temperature in the range of −30 to 100° C., preferably in the range of −10° C. to 50° C.

Preferably the process is carried out under a substantially oxygen free atmosphere for example under nitrogen or under argon. The process may be carried out under pressure in the range of 1 to 5 atmospheres. Preferably the reaction is carried out at atmospheric pressure.

Suitably the molar ratio of compound II to compound III is in the range 0.5:1 to 1:1.5. Preferably the molar ratio is approximately 0.8:1 to 1:1.2. More preferably the molar ratio is approximately 0.9:1. Suitably the methylamine is present in excess. Preferably 1 to 20 molar equivalents of methylamine are used with respect to the compound of formula III. More preferably at least 3 molar equivalents of methylamine are used when a salt of the compound of formula III is used. Most preferably 3–12 molar equivalents of methylamine are used.

Optionally the compound of formula I may be converted into a pharmaceutically acceptable salt thereof by an additional step in which the compound of formula I is brought into contact with an acid by methods known to those skilled in the art. Preferably nizatidine is reacted with hydrochloric acid to give the hydrochloride salt. those skilled in the art. Preferably nizatidine is reacted with hydrochloric acid to give the hydrochloride salt.

The invention is illustrated by the following non-limitative Examples. Novel compounds were characterised by Elemental Analysis and one or more of the following spectroscopic techniques; nuclear magnetic resonance, infra-red and mass spectroscopy. Unless otherwise stated the starting materials used in the examples are commercially available and may be obtained by reference to the Fine Chemicals Directory. 2-Nitromethylenethiazolidine may be obtained from Fine Organics, Seal Sands, Teeside.

EXAMPLE 1

A mixture of 2-nitromethylenethiazolidine (25.7 g) and acetonitrile (50 ml) was stirred and heated at 40° C. under nitrogen. Methylamine gas (16.0 g) was passed into the stirred mixture over 45 minutes to give a solution. A slurry of 4-chloromethyl-2-dimethylaminomethylthiazole hydrochloride (40.0 g) (prepared as described in EP49618) in acetonitrile (50 ml) was added to the solution over a period of 4.5 hours whilst methylamine gas was bubbled through the reaction mixture such that methylamine (38.3 g) was added over the period (total methylamine added was 54.3 g). The temperature of the reaction mixture varied between 24 and 35° C. during the addition. After the addition, the mixture was diluted with acetonitrile (50 ml) and stirred at ambient temperature for 17 hours. A solid was removed by filtration and the filtrate was split into 2 equal portions.

Portion 1

The solution was evaporated to give a black oil which was partitioned between water (200 ml) and chloroform (200 ml). The separated chloroform phase was washed with saturated brine, then dried over magnesium sulphate, filtered and evaporated to give a reddish oil which was dissolved in acetone (200 ml), boiled under reflux, cooled to 40° C., and then seeded with nizatidine. The mixture was left to stand at 0–5° C. for 64 hours. The mixture was filtered to give nizatidine (10.4 g, 37%) m.p. 118–122° C. The structure was confirmed by $^1$H nmr. The product was 95.4% pure by HPLC.

Portion 2

The mixture was evaporated to give an oil which was taken up in chloroform (200 ml) then washed with water (100 ml). The chloroform solution was washed with brine (100 ml), dried over magnesium sulphate, and then concentrated under reduced pressure at 45° C. to give a brown oil. The oil was dissolved in acetone (200 ml) and activated charcoal (0.5 g) was added to the solution. The mixture was boiled under reflux for 10 minutes, then cooled to 45° C. and filtered at this temperature to remove the charcoal. The filtrate was cooled to 20° C., seeded with nizatidine (0.05 g), then cooled 0–5° C. for 45 minutes during which time crystallisation occurred. The mixture was filtered to give nizatidine (9.4 g, 32.2%) Found: C, 43.5; H, 6.25; N, 20.8; S, 19.3%. $C_{12}H_{21}N_5O_2S_2$ requires: C, 43.5; H, 6.4; N, 21.1; S, 19.3%.

EXAMPLE 2

A mixture of 2-nitromethylenethiazolidine (12.6 g) and acetonitrile (21.5 ml) was stirred and heated at 40° C. under argon. Methylamine (20.0 g of a 40% w/w aqueous solution) was added slowly over 30 minutes to the reaction mixture at 40° C. The mixture was cooled at ambient temperature and further methylamine (23.6 g of 40% w/w aqueous solution) was added over 2.5 hours and a solution of 4-chloromethyl-2-dimethylaminomethylthiazole dihydrochloride (25.0 g) in water (30 ml) was added over 5.5 hours with the addition of the thiazole starting simultaneously with the addition of the methylamine. The reaction mixture was left to stir for a further 15 minutes and then was concentrated under reduced pressure. The solid obtained was dissolved in methyl ethyl ketone (130 ml) and aqueous potassium carbonate solution (43 ml, 10% w/w). A further portion of methyl ethyl ketone and water (50 ml) was added to aid dissolution. The mixture was warmed slightly to obtain a solution. The mixture was separated and the aqueous layer was washed with methyl ethyl ketone (2×130 ml and then 1×50 ml). The combined organic layers were dried and evaporated under reduced pressure to yield crude nizatidine (approximately 25 g, 88% yield), which was shown to be 93.7% pure by HPLC. The crude solid was dissolved in dichloromethane (300 ml). The solution was washed with water (3×75 ml). The combined aqueous layer and the washings were back extracted with dichloromethane and the combined organic layers were concentrated under reduced pressure to give nizatidine (21.8 g, 76.8% yield) which was shown to be 98.3% pure by HPLC. The solid was dissolved in ethanol (45 ml) by warming on a steam bath. The solution was removed from the steam bath, treated with activated charcoal (2.3 g) and the mixture was boiled for a further 8 minutes. The mixture was hot filtered. The filtrate was cooled and filtered to give nizatidine (15.6 g, 55% yield) which was shown to be 99.7% pure by HPLC.

EXAMPLE 3

A mixture of 2-nitromethylenethiazolidine (12.6 g) and water (30.0 ml) was stirred and heated at 40° C. under Argon. Methylamine (20.0 g of a 40% w/w aqueous solution) was added slowly over 30 minutes to the reaction mixture at 40° C. The mixture was cooled at ambient temperature and further methylamine (23.6 g of 40% w/w aqueous solution) was added over 2.5 hours and a solution of 4-chloromethyl-2-dimethylaminomethylthiazole dihydrochloride (25.0 g) in water (30 ml) was added over 5.5 hours with the addition of the thiazole starting simultaneously with the addition of the methylamine. The reaction mixture was left to stir for a further 15 minutes and then was concentrated under reduced pressure. The solid obtained was dissolved in a mixture of methyl ethyl ketone (200 ml), aqueous potassium carbonate solution (43 ml, 10% w/w). The mixture was warmed slightly to obtain a solution. The mixture was separated and the aqueous layer was washed with methyl ethyl ketone (2×130 ml and then 1×100 ml). The combined organic layers were evaporated under reduced pressure to yield crude nizatidine (approximately 25.2 g), which was shown to be 89.4% pure by HPLC. The crude solid was dissolved in dichloromethane (300 ml). The solution was washed with water (3×75 ml). The combined aqueous layer and the washings were back extracted with dichloromethane and the combined organic layers were dried and concentrated under reduced pressure to give nizatidine (21.1 g, 74.3% yield). The solid was dissolved in ethanol (45 ml) by warming on a steam bath. The solution was removed from the steam bath treated with activated charcoal (2.3 g) and the mixture was boiled for a further 8 minutes. The mixture was hot filtered. The filtrate was cooled and filtered to give nizatidine (13.8 g, 48% yield) which was shown to be 99.8% pure by HPLC.

EXAMPLE 4

A mixture of 2-nitromethylenethiazolidine (11.95 g) and acetonitrile (154 ml) was stirred and heated at 40° C. and then methylamine (31.7 ml of a 40% w/w aqueous solution) was added in one batch. A solution of 4-chloromethyl-2-dimethylaminomethylthiazole dihydrochloride (21.5 g) in water (21.5 ml) was added dropwise to the reaction mixture over 50 minutes. The mixture was then stirred for 2.5 hours and then the solvent was removed under reduced pressure to give an oil. The oil was dissolved in water (150 ml) and extracted with dichloromethane (3×150 ml). The combined extracts were dried and evaporated to give nizatidine (19.2 g, 70.6% yield). The crude material was 86.8% pure by HPLC.

What is claimed is:

1. A process for the preparation of nizatidine I

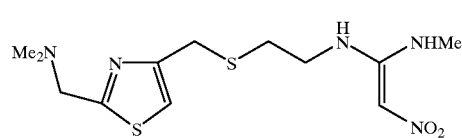

and pharmaceutically acceptable salts thereof, comprising reacting a compound of formula II

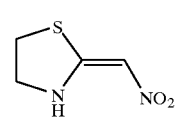

with a compound of formula III

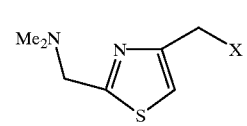

or a salt thereof,
in which X represents a leaving group, in the presence of methylamine in the presence of an inert diluent.

2. A process according to claim 1 in which II is combined with methylamine to give a mixture and III or a salt thereof is added to the mixture.

3. A process according to claim 2 in which further methylamine is added as III or a salt thereof is added to the mixture.

4. A process according to claim 1 in which the inert diluent is acetonitrile or water or mixtures thereof.

5. A process according to a claim 1 in which X represents halo, mesyloxy or tosyloxy.

6. A process according to claim 1 in which the process is carried out at a temperature in the range of −10° C. to 50° C.

7. A process according to claim 1 in which the molar ratio of compound II to compound III is in the range 0.5:1 to 1:1.5.

8. A process according to claim 1 in which 1 to 20 molar equivalents of methylamine are used with respect to the compound of formula III.

* * * * *